United States Patent
Tilghman et al.

[11] Patent Number: 5,139,497
[45] Date of Patent: Aug. 18, 1992

[54] ORBITAL REPAIR IMPLANT

[75] Inventors: Donald M. Tilghman, Pasadena, Md.; Frank H. Morgan, Las Vegas, Nev.

[73] Assignee: TiMesh, Inc., Las Vegas, Nev.

[21] Appl. No.: 797,372

[22] Filed: Nov. 25, 1991

[51] Int. Cl.$^5$ ................ A61B 17/56; A61B 17/58; A61F 2/28; A61F 2/30

[52] U.S. Cl. .................................. 606/69; 606/60; 606/70; 623/16; 623/18

[58] Field of Search ................ 606/60, 61, 69–71; 623/16, 18, 21–23

[56] References Cited

U.S. PATENT DOCUMENTS

| | | | |
|---|---|---|---|
| 3,710,789 | 1/1973 | Ersek | 606/60 |
| 3,720,959 | 3/1973 | Hahn | 623/16 |
| 3,849,805 | 11/1974 | Leake et al. | 623/16 |
| 4,186,448 | 2/1980 | Brekke | 623/16 |
| 4,923,471 | 5/1990 | Morgan | 623/16 |

FOREIGN PATENT DOCUMENTS 0290138 11/1988 European Pat. Off. ............. 606/69

Primary Examiner—Ronald Frinks
Attorney, Agent, or Firm—Philip D. Junkins

[57] ABSTRACT

A biocompatible and pliable metallic surgical implant plate for use in the repair and rigid fixation of internal fractures of the floor and walls of the orbit. The implant plate includes an elongated base portion which is compliant for shaping to interface with the rim structure of the orbit. Three perforated leaf portions, spaced from one-another, project rearwardly from the elongated base portion. The central leaf portion is compliant for shaping to conform to the configuration of the orbit floor, one of the outboard leaf portions is compliant for shaping to conform to the medial wall of the orbit and the other outboard leaf portion is compliant for shaping to conform to the lateral wall of the orbit.

Attachment legs, including screw holes, project forwardly from the elongated base portion of the implant plate and are compliant for shaping and fitment to the anterior face of the rim structure of the orbit with the implant plate being affixed to the rim structure of the orbit by bone screws applied through the screw holes of the attachment legs. Alternatively, an orbital rim reinforcing bar, including screw holes, may be attached to the elongated base portion of the implant plate by a series of legs. The leaf portions of the implant plate may be provided with a thin coating of biocompatible synthetic sheathing material to inhibit the ingrowth of hard and soft tissue into the perforation of the leaf portions.

10 Claims, 1 Drawing Sheet

ORBITAL REPAIR IMPLANT

FIELD OF THE INVENTION

The present invention relates to perforated metallic plates for use in the rigid fixation of internal orbital fractures and continuity defects of the orbit secondary to congenital, developmental, pathological or other acquired etiologies.

BACKGROUND OF THE INVENTION

Bone fracture is a traumatic disruption of the continuity of the bone structure. If there is relative motion of the bone fragments at the fracture site, proper alignment and rejoinder of bone fragments may not be achieved, and the time of fracture healing is usually extended. Disruptions from congenital defects or fractures of the complex and relatively thin bone structures surrounding and supporting the human eye or globe present difficult internal bone repair and fixation problems in reconstructive surgery and in trauma surgery.

The so-called orbital margin comprises a protective bone boundary for the globe. The margin is stronger than the bone structure which forms the orbital walls. If the eye is struck with a relatively round object, i.e., a baseball, a tennis ball, an elbow or a fist, the margin or rim of the orbit, which can withstand considerable force, diffuses the object's impact. However, compression of the orbital contents may occur and produce a "blow-out" fracture of the orbit involving the floor and/or the lateral and medial orbital walls and may result in major destruction of the entire orbit. Also, direct injury at the lateral orbital rim may produce a "tripod" fracture. When significant portions of the internal orbit are disrupted, standard bone-grafting techniques for immediate and post-trauma orbital reconstruction may not result in predictable eye (globe) function and positioning. Critical bone support of the globe by bone-grafting is frequently deficient as a result of bone graft displacement, undercorrection, over correction, or inadequate initial reconstruction of the orbital volume, or ultimate bone-graft resorption.

The superior wall or roof of the orbit is triangular in shape and is formed of two bones. The bulk of the orbital roof consists of the orbital plate of the frontal bone with the lesser wing of the sphenoid making up the posterior portion. The anterior one-half of the orbital roof is relatively thick and forms the floor of the frontal sinus. Posteriorly, the roof of the orbit is thinner and is joined to the medial wall by the frontoethmoidal suture. The orbit roof is separated from the lateral wall of the orbit by the zygomaticofrontal suture anteriorly and the superior orbital fissure posteriorly.

The medial orbital wall is oblong in shape, and is comprised of four bones, i.e., the frontal process of the maxilla, the lacrimal bone, the lamina papyracea of the ethmoid, and the sphenoid. The bulk of the medial wall consists of the very thin and delicate lamina papyracea. Anteriorly, the medial wall of the orbit consists of the maxillary process of the frontal bone and the fossa for the lacrimal sac. The fossa for the lacrimal sac is formed by the frontal process of the maxilla and the lacrimal bone. The lacrimal bone is divided into two portions by a vertical ridge, the posterior lacrimal crests. Posterior to the crest, the lacrimal bone is flat and articulates with the lamina papyracea and the ethmoidal air cells. Anterior to the posterior lacrimal crest, the lacrimal bone becomes thinner and forms a portion of the fossa for the lacrimal sac. The anterior portion of the fossa for the lacrimal sac is formed by the frontal process of the maxilla, which forms the anterior lacrimal crest. The posterior aspects of the medial orbital wall is comprised of a portion of the body of the sphenoid bone.

The inferior orbital wall or floor is comprised of three bones, i.e., the maxilla, the zygomatic, and the palatine. The majority of the orbital floor is formed by the orbital plate of the maxilla. The shape of the inferior orbital wall or floor approximates an equilateral triangle. The orbital floor extends only about two-thirds of the depth of the orbit and does not extend to the orbital apex. The inferior orbital rim and the adjacent anterior portion of the orbital floor are strong in comparison to the thinner portions of the orbital floor. It is not surprising that a traumatic blunt force applied to the orbit compresses the orbital contents and often results in fracture of the orbital floor.

The lateral orbital wall is triangular in shape and is comprised of the zygomatic bone and the greater wing of the sphenoid. In the posterior orbit, the boundaries of the lateral orbit wall are defined by the superior and inferior orbital fissures. The lateral orbital wall is flat and is directed at a 45 degree angle from the medial orbital wall. The lateral orbital wall is the strongest of the orbital walls due to the prominent zygomatic bone but presents a series of alternating strong and weak areas.

As has been noted above, fractures of the internal orbit are commonly seen as the result of blunt force blows or trauma to the face. These fractures may occur as isolated blow-outs or may be associated with multiple facial fractures. The degree of destruction of the internal orbit may range from a small defect in the floor to destruction of all four walls of the orbit. The recommended treatment of these injuries varies greatly. Surgical treatment has ranged from packing of the maxillary antrum to total orbital reconstruction with autogenous or synthetic materials. Accurate anatomical reconstruction of the bony orbit is essential to maintain normal function and appearance of the eye following orbital fractures. Because most of the bone in the internal orbit is thin, it is frequently difficult to reduce and adequately stabilize the fractured bone fragments without the use of autogenous or alloplastic materials.

Historically autogenous bone grafts have been the material of choice for most craniomaxillofacial surgeons for the reconstruction of the internal orbit. Split membranous bone from the calvarium and other autogenous materials including iliac bone, split rib bone and catrilage have been used as bone graft materials. Such materials, however, have yielded an unpredictable amount of resorption, particularly in the posterior half of the orbit. When significant resorption occurs, there is increased displacement of the globe.

A variety of alloplastic materials such as silicone ribber, Teflon, Supramid, tantalum mesh, Vitallium mesh, titanium mesh, polyethylene, and methyl methacrylate have been used for orbital reconstruction. Over the past ten years there has been an increasing interest in, and use of, perforated biocompatible metallic strips and panels as a means for rigid internal fixation of fractures in trauma surgery and as a plate material for bone part immobilization and stablilization and bone graft support material in reconstructive surgery. Of particular interest has been the use of perforated strips and panels fabricated of totanium as an unequaled implant material in use clinically for over 30 years with no documented cases of adverse reactions. Pure titanium is the material of choice in craniofacial reconstructive surgery when non-removal of the implant is indicated. As an implant material, pure titanium is preferred because its low density (weight) and elastic modules (stiffness) are approximately one-half that of stainless steel or cobalt-chromium alloys and the material is corrosion resistant and pliable. Further, bone plates made of perforated titanium strips and perforated titanium panels can be cut to appropriate configuration and contoured at the time of surgery and, when affixed to bone fragments or bone parts with bone screws, provide solid, stable fixation means during trauma surgery and planned reconstructive surgery.

A preferred form of perforated titanium strips and panels (titanium mesh) includes rows of substantially square perforations which are formed in titanium sheet material. The use of titanium mesh with square holes for internal fixation of bone fractures and for reconstructive surgery provides the surgeon with an implantable plate material which can be easily cut to desired contour and shaped or bent to conform to bone fracture and reconstruction sites.

It is a principal object of the present invention to provide a unique perforated metallic plate structure for the internal repair of orbital defects and fixation of orbital fractures.

It is a further object of the invention to provide a unique perforated metallic implantable plate structure which is preshaped and ready for use in surgical procedures relating to the repair of the medial and lateral walls and the floor of the orbit.

It is still a further object of the invention to provide a unique orbital repair implant plate structure of preshaped contour for use in the surgical internal fixation of orbital fractures.

It is yet another object of the invention to provide a perforated metallic orbital repair implant structure of preshaped configuration which can be readily cut, reshaped or bent to conform to the orbital walls and affixed to the orbital margin or rim.

Other objects and advantages of the invention will be apparent from the following summary and detailed description of the orbital repair implant structure of the invention taken with the accompanying drawing figures.

SUMMARY OF THE INVENTION

The present invention relates to an improved orbital repair implant formed of perforated biocompatible metallic sheet material. The orbital repair implant of the invention is fabricated of a metal or metallic alloy such as titanium, titanium alloys, cobalt-chrome alloys and stainless steel (preferably fabricated from pure pliable titanium sheet material having a thickness of about 0.2 mm to about 0.5 mm) and includes an implant base or forward portion from which project rearwardly three perforated leaf portions. The leaf potions or perforated implant leaves and base or forward portion of the implant may be contoured or bent by plate bending pliers or contour forceps. The implant leaves are arranged so that upon contouring an implant, so as to fit the orbit of a patient requiring surgical reconstruction, the central leaf covers and interfaces the bone structure of the orbit floor whereas the outer leaves cover and interface the bone structures of the medial and lateral orbital walls. The leaves of the orbital repair implant of the invention are spaced from one-another whereby between the central leaf and the medial leaf there exists an open area so the implant clears the lacrimal (tear) duct of the orbit structure and whereby between the central leaf and the lateral leaf there exists an open area so that the implant clears the orbital fissure.

To the base or forward portion of the orbital implant there is integrally formed a series of attachment tabs which include outer screw rings or, alternatively, a series of legs to which an orbital rim reinforcing bar is attached and which includes screw holes. With the orbital implant appropriately contoured (bent) for insertion into the orbital cavity, the attachment tabs or attachment legs and bar are contoured (bent) downwardly for fitment to the bone of the orbital rim and affixation thereto via bone screws applied through the screw holes of the attachment tabs or attachment bar.

The perforated leaves of the implant each include a peripheral margin area which can be trimmed by a cutting tool so that the implant properly fits the patient's orbit undergoing reconstruction. Also, one or more of the attachment tabs or portions of the attachment bar may be removed by a cutting tool to conform the implant to the size and structure of the frontal bone of the orbit. Where the orbit reconstruction is related to only the orbit floor or to the medial or lateral walls, unused implant leaves and/or attachment tabs or portions of the attachment bar may be removed by a cutting tool.

The basic implant structure of the invention may include a medial leaf notch so that such leaf clears the medial canthal ligament and the leaf periphery area surrounding such notch may include holes for receiving sutures for securing the canthal ligament to the implant structure. Further, additional suture holes may be incorporated into the implant structure for securing the orbital structures and/or muscle forms to the implant.

Reconstruction of the internal orbit, after implant placement and affixation, can be completed by inserting bone grafts over the orbital floor to adjust the volume of the orbit and the level of the globe. Split rib, calvarial or iliac bone grafts may be used. Soft and hard tissue ingrowth into the perforations of the implant leaves is to be expected. The implant leaves may be coated with a biocompatible and sterilizable synthetic sheathing material, such as silicone rubber or compliant urethane compounds, to add thickness to the implant and to blunt the edges thereof with respect to the soft structures of the orbit, and so that soft and hard tissue ingrowth into the implant perforations is inhibited.

BRIEF DESCRIPTION OF THE DRAWING FIGURES

DETAILED DESCRIPTION OF THE INVENTION

Figure 1:
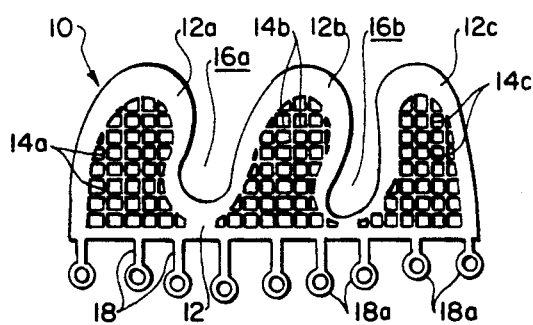
FIG. 1 is a top plan view of a perforated metallic plate orbital repair implant in accordance with the present invention.

Referring to FIG. 1 of the drawing sheet, there is illustrated an improved orbital repair implant 10 formed of perforated biocompatible metallic sheet material, in accordance with the invention. The orbital repair implant 10 is fabricated from a sheet of relatively thin (stress free) pliable, biocompatible metal or metal alloy (preferably titanium). The implant includes a base or forward portion 12 from which project posteriorly (rearwardly) three perforated leaf portions 12a, 12b and 12c. The leaf portions include, respectively, perforation areas or mesh areas 14a, 14b and 14c. The leaf portions are spaced from one-another by open areas 16a and 16b.

Figure 2:
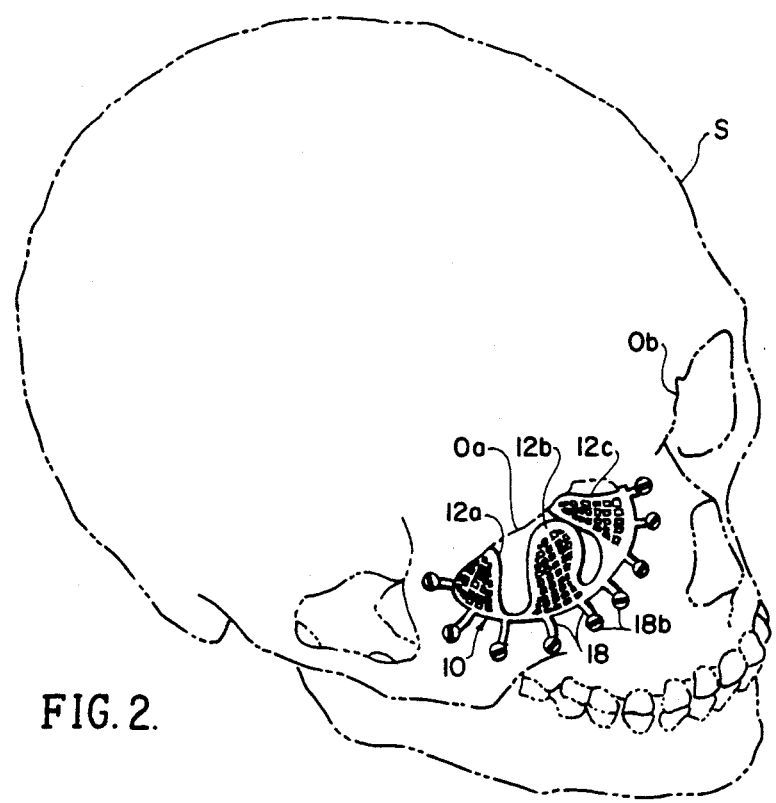
FIG. 2 is perspective view of a human skull in dotted line presentation showing the orbital repair implant of FIG. 1, after appropriate shaping and contouring, in place within the right eye orbit of the skull and affixed to the frontal bone structure of the orbit via bone screws.

As illustrated in FIG. 1 the orbital repair implant 10 is oriented for use in reconstruction of the orbit of the right eye and placement as shown with respect to the human skull S in FIG. 2. Thus, the open area 16a between the central leaf 12b and the lateral leaf 12a provides a space so that when the implant is placed in the right eye orbit the implant clears the orbital fissure. Further, the open area 16b between the central leaf 12b and the medial leaf 12c provides means for flexibility in shaping the implant and allows independent movement of the leaf 12c.

To the base or forward portion 12 of the implant 10 there is integrally formed a series of attachment tabs 18 which include outer screw rings 18a with their respective screw holes. With the orbital implant 10 appropriately contoured (bent) for insertion into the orbital cavity, the attachment tabs are bent downwardly and outwardly for fitment to the lateral, inferior and medial orbital rim. Affixation thereto is via bone screws. As previously indicated, the orbital repair implant of FIG. 1 presents leaf orientation and configuration so that the implant (after appropriate contouring) may be placed in the orbit Oa (right orbit) of the skull S illustrated in dotted line presentation in FIG. 2. The implant is maintained in desired position in the orbital cavity by bone screws 18b applied to the inferior orbital rim through the screw holes in the screw rings 18a of the attachment tabs 18. As previously indicated, one or more of the attachment tabs 18 may be removed by a cutting tool to conform the implant to the size and structure of the orbital rim and the perforated leaves 12a, 12b and 12c of the implant may be trimmed in their peripheral margin areas for proper fitment of the structure to the orbit walls. Further, were the orbit reconstruction surgery is related only to the orbit floor or to the medial or lateral walls, an unneeded implant leaf may be removed by a cutting tool.

Figure 3:
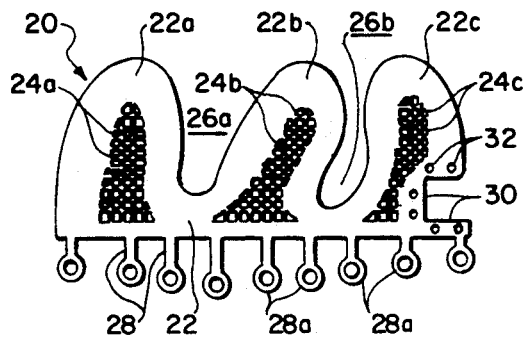
FIG. 3 is a top plan view of an alternative form of a perforated metallic plate orbital repair implant in accordance with the invention showing a notch in the medial leaf thereof to prevent impingement on the medial canthal ligament and nasolacrimal apparatus of the eye.

Referring now to FIG.3 there is illustrated in plan view an alternative form of the perforated metallic plate orbital repair implant of the invention. The implant 20 again is illustrated as oriented and configured for use in repair of the orbit of the right eye of the patient. Thus, the implant 20 includes a base or forward portion 22 from which project laterally three perforated leaf portions 22a (lateral leaf), 22b (central leaf) and 22c (medial leaf). The leaf portions include, respectively, perforation areas or mesh areas 24a, 24b and 24c and the leaves are spaced from one-another leaving required open areas 26a and 26b as previously discussed with respect to the implant illustrated in FIG. 1. Also, the implant 20 includes attachment tabs 28 with associated screw rings 28a affixation of the implant to the frontal bone of the orbit via bone screws. The implant 20 further includes in its medial leaf 22c a medial leaf notch 30 so that such leaf, upon reconstruction placement in the orbit, clears the medial canthal ligament and nasolacrimal apparatus and the leaf (in the periphery area surrounding the leaf notch 30) is provided with holes 32 for receiving sutures for securing the medial canthal ligament to the implant structure.

Figure 4:
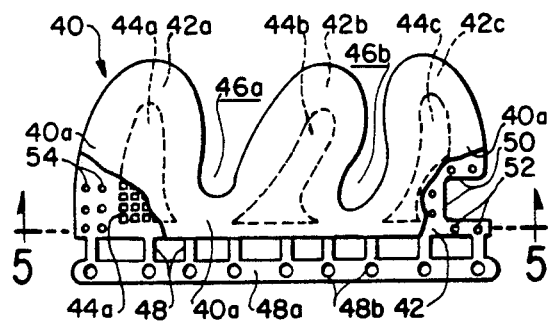
FIG. 4 is a top plan view of the perforated metallic plate orbital repair implant of FIG. 3 with the perforated leaves of the implant coated with a biocompatible plastic material to inhibit the ingrowth of tissue into the perforations of the implant.

In FIG. 4 there is illustrated a further alternative form of the orbital repair implant of the present invention. The implant 40 again is shown as oriented and configured for use in repair of the right orbit of the patient. The implant 40 includes a base or forward portion 42 from which project laterally three perforated leaf portions 42a(lateral leaf), 42b (central leaf) and 42c (medial leaf). The leaf portions include, respectively, perforation areas or mesh areas 44a, 44b and 44c and the leaves are spaced from one-another leaving required open areas 46a and 46b. To the base or forward portion 42 of the implant there is integrally formed a series of legs 48 to which an orbital rim reinforcing bar 48a is attached and provided with screw holes 48b through which bone screws may be applied (after contouring and orbital fitment of the implant structure) for affixation of the implant to the rim of the orbit.

Figure 5:
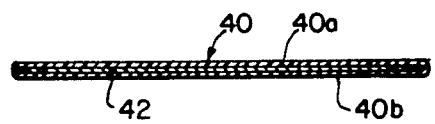
FIG. 5 is a cross-sectional view of the perforated metallic plate orbital repair implant of FIG. 4 taken along line 5—5 of FIG. 4.

The implant 40 of FIG. 4 is also provided, in its base or forward portion 42 and leaf portions 42a, 42b and 42c, with a thin coating 40a of a biocompatible and sterilizable synthetic sheathing material such as silicone rubber or compliant urethane compounds. Such a coating may be applied to one or both plan surfaces of the implant where it is contemplated or expected that the orbital implant of the invention may or will be removed after full or substantial healing and reconstitution of the surrounding orbital bone. The coating material thereby inhibits soft and hard tissue ingrowth into the perforations of the implant leaf portions. FIG. 5 is a cross-sectional view of the perforated metallic plate orbital repair implant 40 of FIG. 4 taken along line 5—5 of FIG. 4 through the forward portion 42 thereof. In such figure the coating of sheathing material is shown on each side of the forward or base portion 42 and the leaf portions 42a, 42b and 42c as coating layers 40a and 40b.

Referring again to FIG. 4, the orbital repair implant 40 includes in its medial leaf 42c a medial leaf notch 50 so that leaf, upon surgical reconstruction placement in the orbit, clears the medial canthal ligament and nasolacrimal apparatus and such leaf (in the peripheral area surrounding the leaf notch 50) is provided with holes 52 for receiving sutures for securing the medial canthal ligament to the implant structure. Further, the lateral leaf 42a of the implant 40, proximate the forward or base portion 42, may be provided with additional holes 54 for attachment of the implant by sutures, as needed, to additional elements of the orbit structure, lateral canthal ligament or muscle forms of the eye.

As previously indicated, reconstruction of the internal orbit, after placement and affixation of the orbital repair implant of the invention, may be completed by inserting bone grafts over the orbital floor and implant mesh structure (or coated implant leaf walls) to alter the volume of the orbit and to adjust the level of the globe. Split rib, calvarial or iliac bone grafts may be used for this purpose. Through use of the biocompatible, perforated metallic implant of the present invention for the internal fixation of bone fractures in the orbital walls and the repair of discontinuity defects, and through the practice of improved surgical methodology permitted by use of such implant, faster and more effective rejoinder and healing of fractured bone fragments and discontinuity defects of the orbit may be achieved and shorter term surgical intervention and orbital bone and muscle exposure is accomplished.

It is to be understood that, while the orbital repair implant plates 10, 20 and 40 of the invention have been shown in the drawings FIGS. 1, 3 and 4 as applicable to repair of the right orbit Oa, by merely turning the implant plate over it becomes applicable to repair of the left orbit Ob. Further, the implant plate may be readily modified, as required, so that it may be used as a single leaf (lateral, central or medial) orbital repair implant or as a 2-leaf orbital repair implant (lateral-central, central-medial or lateral-medial). The implant of the invention is thus adaptable to a wide variety of surgical needs in orbital repair and defect correction by cutting, shaping and trimming at the time of surgery.

While the invention has been described in connection with particular structural embodiments of the orbital repair implant device, many modifications of the invention will be apparent to those skilled in the art. Accordingly, such modifications are to be included within the spirit and scope of the invention as defined by the following claims.

What is claimed is:

1. A biocompatible and pliable metallic surgical implant plate for use in the repair of congenital and acquired defects and the rigid fixation of internal fractures and other defects of the floor and walls of the orbit comprising:
   a) an elongated base portion of said implant plate being compliant for shaping to interface with the rim structure of the orbit floor and the rim structure of the medial and lateral walls of the orbit;
   b) three perforated leaf portions of said implant plate projecting rearwardly from the elongated base portion thereof, said leaf portions being spaced from one-another, the central leaf portion being compliant for shaping to conform to the configuration of the orbit floor, one of the outboard leaf portions being compliant for shaping to conform to the medial wall of the orbit and the other of said outboard leaf portions being compliant for shaping to conform to the lateral wall of the orbit; and
   c) attachment means for said implant plate projecting forwardly from the elongated base portion thereof and being compliant for shaping and fitment to the anterior face of the rim structure of the orbit, said attachment means including screw holes through which may be applied bone screws threaded into the rim structure of the orbit for fixation of said implant plate therein.

2. A biocompatible and pliable metallic surgical implant plate for use in the repair of congenital and acquired defects and the rigid fixation of internal fractures and other defects of the floor and walls of the orbit as claimed in claim 1 wherein the leaf portions of said implant plate each include a central open mesh area providing the perforations of said portions.

3. A biocompatible and pliable metallic surgical implant plate for use in the repair of congenital and acquired defects and the rigid fixation of internal fractures and other defects of the floor and walls of the orbit as claimed in claim 2 wherein the leaf portions of said implant plate each include a peripheral margin area surrounding said central mesh area providing a leaf surface area for trimming to final dimension and configuration for fitment to the orbit.

4. A biocompatible and pliable metallic surgical implant plate for use in the repair of congenital and acquired defects and the rigid fixation of internal fractures and other defects of the floor and walls of the orbit as claimed in claim 1 wherein the outboard leaf portion of said implant plate shaped to conform to the medial wall of the orbit includes a notch whereby said leaf upon placement in the orbit clears the medial canthal ligament and lacrimal apparatus of the orbit and the peripheral area of said leaf surrounding said notch includes holes for receiving sutures for securing the medial canthal ligament to said implant plate.

5. A biocompatible and piable metallic surgical implant plate for use in the repair of congenital and acquired defects and the rigid fixation of internal fractures and other defects of the floor and walls of the orbit as claimed in claim 1 wherein the outboard leaf portion of said implant plate shaped to conform to the lateral wall of the orbit includes holes for receiving sutures for securing the lateral canthal ligament and muscle forms associated with the lateral wall of the orbit to said implant plate.

6. A biocompatible and pliable metallic surgical implant plate for use in the repair of congenital and acquired defects and the rigid fixation of internal fractures and other defects of the floor and walls of the orbit as claimed in claim 1 wherein the elongated base portion and the perforated leaf portions of said implant plate are provided with a thin coating of biocompatible and sterilizable synthetic sheathing material to inhibit the ingrowth of hard and soft tissue into the perforation of the leaf portions of said implant whereby said implant plate may be removed from its placement position in the orbit.

7. A biocompatible and pliable metallic surgical implant plate for use in the repair of congenital and acquired defects and the rigid fixation of internal fractures and other defects of the floor and walls of the orbit as claimed in claim 6 wherein said sheathing material is selected from the group of biocompatible materials consisting of silicone rubber and compliant urethane compounds.

8. A biocompatible and pliable metallic surgical implant plate for use in the repair of congenital and acquired defects and the rigid fixation of internal fractures and other defects of the floor and walls of the orbit as claimed in claim 1 wherein the attachment means for said implant plate comprises a series of attachment tabs projecting forwardly from the elongated base portion of said implant plate and spaced along said base portion, each of said tabs terminating in a screw ring providing a screw hole through which may be applied a bone screw for threading into the rim of the orbit and surrounding bone.

9. A biocompatible and pliable metallic surgical implant plate for use in the repair of congenital and acquired defects and the rigid fixation of internal fractures and other defects of the floor and walls of the orbit as claimed in claim 1 wherein the attachment means for said implant plate comprises an orbital rim reinforcing bar attached to and spaced from the elongated base portion of said implant plate by a series of legs spaced along said base portion, said reinforcing bar including a series of screw holes through which may be applied bone screws for threading into the rim of the orbit.

10. A biocompatible and pliable metallic surgical implant plate for use in the repair of congenital and acquired defects and the rigid fixation of internal fractures and other defects of the floor and walls of the orbit as claimed in claim 1 wherein said plate, including its base portion, leaf portions and attachment means, is fabricated of a metal or metallic alloy selected from the group consisting of titanium, titanium alloys, cobalt-chrome alloys and stainless steel.

* * * * *